United States Patent
Suzukamo et al.

(10) Patent No.: US 6,469,198 B2
(45) Date of Patent: Oct. 22, 2002

(54) CHIRAL COPPER COMPLEX CATALYST COMPOSITION AND ASYMMETRIC PRODUCTION PROCESS USING THE SAME

(75) Inventors: Gohfu Suzukamo, Suita; Makoto Itagaki, Takatsuki; Michio Yamamoto, Otsu, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/766,579

(22) Filed: Jan. 23, 2001

(65) Prior Publication Data

US 2001/0037036 A1 Nov. 1, 2001

(30) Foreign Application Priority Data

Jan. 25, 2000 (JP) ........................... 2000-016279
Jan. 27, 2000 (JP) ........................... 2000-018595

(51) Int. Cl.⁷ .............................................. C07C 69/74
(52) U.S. Cl. ...................... 560/124; 560/102; 560/118; 560/176; 560/101
(58) Field of Search .............................. 560/124, 102, 560/101, 116, 118

(56) References Cited

U.S. PATENT DOCUMENTS

| | | |
|---|---|---|
| 3,868,401 A | 2/1975 | Aratani et al. |
| 4,029,683 A | 6/1977 | Aratani et al. |
| 4,029,690 A | 6/1977 | Aratani et al. |
| 4,197,408 A * | 4/1980 | Aratari et al. |
| 4,552,972 A * | 11/1985 | Aratari et al. |
| 4,603,218 A * | 7/1986 | Aratari et al. |

FOREIGN PATENT DOCUMENTS

| | | |
|---|---|---|
| EP | 0 128 012 A2 | 12/1984 |
| GB | 1 455 189 | 11/1976 |
| JP | 5473758 A | 6/1979 |

OTHER PUBLICATIONS

F. Dammast et al., Chem. Ber. 126 (11), 2449–2456 (1993) (English Abstract included).

K. Tanaka et al., Chem. Pharm. Bull. 27 (5) 1245–1251 (1979).

Zhengning Li et al.; Tetrahedron: Asymmetry 11 (2000) pp. 1157–1163.

Zhengning Li et al., Tetrahedron 56 (2000) pp. 7187–7191.

Tadatoshi Aratani; Pure & Appl. Chem., vol. 57, No. 12, (1985) pp. 1839–1844.

\* cited by examiner

*Primary Examiner*—Paul J. Killos
*Assistant Examiner*—Hector Reyes
(74) *Attorney, Agent, or Firm*—Birch, Stewart, Kolasch & Birch, LLP

(57) ABSTRACT

There is disclosed chiral copper complex catalyst composition, which is obtained by contacting an optically active N-salicylideneaminoalcohol compound of formula (1):

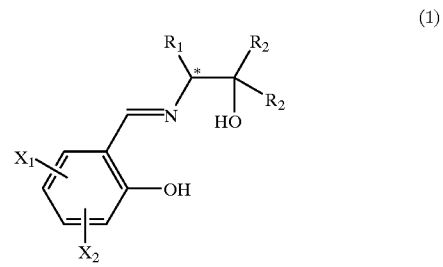

with a mono-valent or di-valent copper compound in an inert solvent, wherein $R_1$ and $R_2$ represent an alkyl group and the like, $X_1$ and $X_2$ represent a hydrogen atom, a halogen atom, a nitro group, an alkyl group, an alkoxy group, a cyano group or the like, and the amount of the mono-valent or di-valent copper compound is less than 1 mole per 1 mole of the optically active N-salicylideneaminoalcohol compound of formula (1), and a process for producing an optically active cylopropane-carboxylic acid ester using the same.

10 Claims, No Drawings

CHIRAL COPPER COMPLEX CATALYST COMPOSITION AND ASYMMETRIC PRODUCTION PROCESS USING THE SAME

FIELD OF THE INVENTION

The present invention relates to a production process for asymmetric synthesis of cyclopropane-carboxylic acid compound using a chiral copper complex catalyst.

BACKGROUND OF THE INVENTION

As a process for producing an optically active cyclopropanecarboxylic acid ester derivative, there has been reported a process of using a chiral copper complex catalyst which was prepared by reacting equivalent or excess amount of cupric salt with optically active salicylideneaminoalcohol (JP-B 53-43955, JP-A 50-151842, JP-A 54-73758 and JP-A 59-225194).

However, in the disclosed processes said copper complex required purification by recrystallization or washing with methanol or the like to remove an excessive amount of copper compound.

SUMMARY OF THE INVENTION

According to the present invention, a chiral copper complex catalyst composition can be obtained in an industrially advantageously and can be used in an asymmetric cyclopropanation reaction with good reproducibility.

The present invention provides:
1. a chiral copper complex catalyst composition, which is obtained by contacting an optically active N-salicylideneaminoalcohol compound of formula (1):

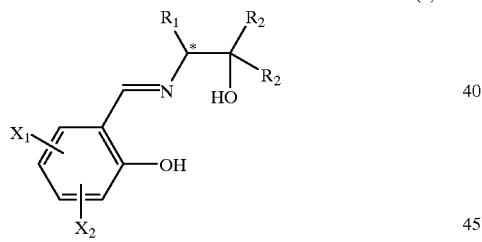

(1)

with a mono-valent or di-valent copper compound in an inert solvent,
wherein $R_1$ represents
an alkyl group which may be substituted with a group selected from an alkoxy group, an aralkyloxy group, an aryloxy group, and cycloalkoxy group,
an aralkyl, aryl or cycloalkyl group all of which may be substituted with a group selected from an alkyl group, an alkoxy group, an aralkyloxy group, an aryloxy group, and a cycloalkoxy group,
$R_2$ represent
a hydrogen atom, an alkyl group, a cycloalkyl group, or an aralkyl or phenyl group which may be substituted with a group selected from an alkyl group, an alkoxy group, an aralkyloxy group, an aryloxy group, and a cycloalkoxy group,
$X_1$ and $X_2$ are the same or different and independently represent a hydrogen atom, a halogen atom, a nitro group, an alkyl group, an alkoxy group or a cyano group, and two adjacent $X_1$ and $X_2$ together with the benzene ring to which they are bonded may form a 1-hydroxy-2- or 2-hydroxy-1-naphthyl group, and
the carbon atom denoted by "*" is an asymmetric carbon atom having either an S or R configuration, and
the amount of the mono-valent or di-valent copper compound is less than 1 mole per 1 mole of the optically active N-salicylideneaminoalcohol compound of formula (1), and 2. a process for producing an optically active cyclopropane-carboxylic acid ester of formula (2):

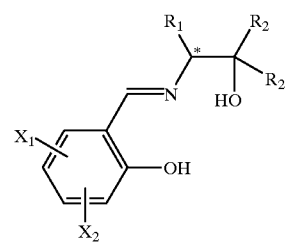

(2)

wherein $R_3$, $R_4$, $R_5$ and $R_6$ are as defined below, and $R_7$ represents
an alkyl group having 1 to 8 carbon atoms,
a cycloalkyl group which may be optionally substituted with a lower alkyl group,
a benzyl group or phenyl group which may be optionally substituted with a lower alkyl group, a lower alkoxy group or a phenoxy group,
which comprises the steps of:
(a) contacting an optically active N-salicylideneaminoalcohol compound of formula (1):

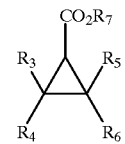

(1)

with a mono-valent or di-valent copper compound in an inert solvent,
wherein $R_1$, $R_2$, $X_1$, $X_2$ and "*" have the same meanings as defined above, and the amount of the mono-valent or di-valent copper compound is less than 1 mole per 1 mole of the optically active N-salicylideneaminoalcohol compound of formula (1), and (b) reacting a prochiral olefin of formula (3):

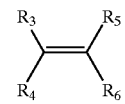

(3)

wherein $R_3$, $R_4$, $R_5$ and $R_6$ independently represent a
hydrogen atom,
a halogen atom,
a (C1–C10)alkyl group which may be substituted with a halogen atom or a lower alkoxy group,
a (C4–C8)cycloalkyl group,
an aryl group which may be substituted with a halogen atom, a lower
alkyl group, or a lower alkoxy group,
$R_3$ and $R_4$, or $R_5$ and $R_6$ may be bonded at their terminals to form an
alkylene group having 2–4 carbon atoms, and
one of $R_3$, $R_4$, $R_5$ and $R_6$ groups represents an alkenyl group which may be substituted with a halogen atom, an alkoxy group or an alkoxy carbonyl group, of which alkoxy may be substituted with a halogen atom or atoms provided that when $R_3$ and $R_5$ are the same, $R_4$ and $R_6$ are not the same,
with a diazoacetic acid ester of formula (4):

N$_2$CHCO$_2$R$_7$ (4)

wherein $R_7$ is the same as defined above, in the presence of a chiral copper complex catalyst composition so produced in step (a).

DETAILED DESCRIPTION

First, a description will be made to the optically active salicylideneaminoalcohol compound of formula (1) as defined above.

Examples of the alkyl group which may be substituted with a group selected from an alkoxy group, an aralkyloxy group, an aryloxy group and a cycloalkoxy group, represented by $R_1$, include
a (C1–C8)alkyl group (e.g., a methyl, ethyl, n-propyl, i-propyl, n-butyl, i-butyl, sec-butyl, t-butyl, n-pentyl, n-hexyl, n-pentyl, n-octyl, n-nonyl, or n-decyl group) which may be substituted with a group selected from
a (C1–C4)alkoxy group(e.g., a methoxy, ethoxy, n-propoxy, i-propoxy, n-butoxy, i-butoxy, sec-butoxy or t-butoxy group),
a (C7–C11)aralkyloxy group(e.g., a benzyloxy or naphthylmethyloxy group),
a (C6–C11)aryloxy group(e.g., a phenoxy or naphthoxy group),
a (C4–C6)cycloalkoxy group(e.g., a cyclobutyloxy, cyclopentyloxy or cyclohexyloxy group) and the like.

Examples of the aralkyl group, the aryl group and the cycloalkyl group, all of which may be substituted with a group selected from an alkyl group, an alkoxy group, an aralkyloxy group, an aryloxy group and a cycloalkoxy group include
a (C7–C11)aralkyl group(e.g., a benzyl, or naphthylmethyl group),
a (C6–C10)aryl group(e.g., a phenyl, or naphthyl group),
a (C4–C6)cycloalkyl group(e.g., a cyclobutyl, cyclopentyl, or cyclohexyl group), all of which may be substituted with
the (C1–C8)alkyl, (C7–C11)aralkyloxy, (C6–C11)aryloxy and (C4–C6)cycloalkoxy group as specified above and a (C1–C8)alkoxy group(e.g, a methoxy, ethoxy, n-propoxy, i-propoxy, n-butoxy, i-butoxy, sec-butoxy, t-butoxy, n-pentoxy, n-hexyloxy, n-pentyloxy or n-octyloxy group).

The alkyl group represented by $R_2$ include said (C1–C8) alkyl group as above. The cycloalkyl group represented by $R_2$ include said (C4–C6)cycloalkyl group as above.

The aralkyl or phenyl group which may be substituted with a group elected from an alkyl group, an alkoxy group, an aralkyloxy group, an aryloxy group and a cycloalkoxy group represented by $R_2$ include the same meanings as defined above for the groups represented by $R_1$.

The substituent group $X_1$ and $X_2$ of the salicylideneaminoalcohol compound of formula (1) will be explained below.

Examples of the halogen atom represented by $X_1$ and $X_2$ include a fluorine atom, a chlorine atom and a bromine atom.

Examples of the alkyl group include a (C1–C8) alkyl group such as a methyl, ethyl, n-propyl, i-propyl, n-butyl, t-butyl, sec-butyl, n-pentyl, n-hexyl, n-heptyl, n-octyl and the like.

Examples of the alkoxy group include the same (C1–C4) alkoxy group as defined above in the alkoxy group for $R_1$.

In salicylideneaminoalcohol compound of formula (1), preferred are
a salicylideneaminoalcohol compound (1) in which $X_1$ represents a bromine atom and $X_2$ is a hydrogen atom or a bromine atom,
a salicylideneaminoalcohol compound (1) in which $X_1$ represents a nitro group and $X_2$ is a hydrogen atom, a methyl group or a methoxy group,
a salicylideneaminoalcohol compound (1) in which $X_1$ represents a chlorine atom and $X_2$ is a chlorine atom, and
a salicylideneaminoalcohol compound (1) in which $X_1$ is a hydrogen atom and $X_2$ is a fluorine atom.
More preferred are
a salicylideneaminoalcohol compound (1) in which $X_1$ represents a nitro group or a bromine atom and $X_2$ is a hydrogen atom,
a salicylideneaminoalcohol compound (1) in which $X_1$ represents a chlorine atom and $X_2$ is a chlorine atom, and
a salicylideneaminoalcohol compound (1) in which $X_1$ is a hydrogen atom and $X_2$ is a fluorine atom.

Among the optically active salicylideneaminoalcohol compound of formula (1), $R_1$ is preferably an alkyl group having 1 to 6 carbon atoms, an aralkyl, an aryl group, and $R_2$ is preferably an alkyl group (e.g. lower alkyl groups having 1 to 6 carbon atoms), an aralkyl group (e.g., a benzyl group), an aryl group (e.g., a phenyl group, a 2-methoxyphenyl group, a 2-tert-butoxy-5-tert-butylphenyl group or a 2-octyloxy-5-tert-butylphenyl group).

Specific examples the optically active salicylideneaminoalcohol compound of formula (1) include optically active
N-salicyliden-2-amino-1,1-diphenyl-1-propanol,
N-salicyliden-2-amino-1,1-di(2-methoxyphenyl)-1-propanol,
N-salicyliden-2-amino-1,1-di(2-isopropoxyphenyl)-1-propanol,
N-salicyliden-2-amino-1,1-di(2-butoxy-5-t-butylphenyl)-1-propanol,
N-salicyliden-2-amino-1,1-diphenyl-3-phenyl-1-propanol,
N-salicyliden-2-amino-1,1-di(2-methoxyphenyl)-3-phenyl-1-propanol,
N-salicyliden-2-amino-1,1-di(2-isopropoxyphenyl)-3-phenyl-1-propanol,
N-salicyliden-2-amino-1,1-di(2-butoxy-6-t-butylphenyl)-3-phenyl-1-propanol,
N-salicyliden-2-amino-1,1-di(2-methoxyphenyl)-3-phenyl-1-butanol,
N-(3-fluorosalicyliden)-2-amino-1,1-di(2-butoxy-5-t-butylphenyl)-1-propanol,
N-(3-fluorosalicyliden)-2-amino-1,1-di(2-octyloxy-5-t-butylphenyl)-1-propanol,
N-(3-fluorosalicyliden)-2-amino-1,1-di(2-butoxy-5-t-butylphenyl)-3-phenyl-1-propanol, N-(3-fluorosalicyliden)-2-amino-1,1-di(2-methoxyphenyl)-1-propanol,
N-(3-fluorosalicyliden)-2-amino-1,1-diphenyl-1-propanol,
N-(3-fluorosalicyliden)-2-amino-1,1-di(2-benzyloxy-5-methylphenyl)-3-(4-iso-propoxyphenyl)-1-propanol,
N-(3-fluorosalicyliden)-2-amino-1,1-diphenyl-3-phenyl-1-propanol,
N-(3-fluorosalicyliden)-2-amino-1,1-di(2-methoxyphenyl)-3-methyl-1-butanol,
N-(3-fluorosalicyliden)-2-amino-3-phenyl-1-propanol,
N-(3,5-dichlorosalicylidene)-2-amino-1,1-diphenylpropanol,
N-(3,5-dichlorosalicylidene)-2-amino-1,1-di-(2-methoxyphenyl)propanol
N-(3,5-dichlorosalicylidene)-2-amino-1,1-di(5-tert-butyl-2-tert-butoxyphenyl)-3-phenyl-1-propanol,
N-(3,5-dichlorosalicylidene)-2-amino-1,1-di-(5-tert-butyl-2-octyloxyphenyl)-propanol
N-(5-bromosalicyliden)-2-amino-1,1-diphenyl-1-propanol,
N-(5-bromosalicyliden)-2-amino-1,1-di(2-methoxyphenyl)-1-propanol,
N-(3,5-dibromosalicyliden)-2-amino-1,1-diphenyl-1-propanol,
N-(5-nitrosalicyliden)-2-amino-1,1-diphenyl-1-propanol,
N-(5-nitrosalicyliden)-2-amino-1,1-diphenyl-3-phenyl-1-propanol,
N-(5-nitrosalicyliden)-2-amino-1,1-di(2-butoxy-5-t-butylphenyl)-3-phenyl-propanol,
N-(5-nitrosalicyliden)-2-amino-1,1-di(2-benzyloxy-5-methylphenyl)-3-(4-iso-propoxyphenyl)-1-propanol,
N-(5-nitrosalicyliden)-2-amino-1,1-di(2-methoxyphenyl)-1-propanol,
N-(5-nitrosalicyliden)-2-amino -1,1-di(2-t-butyl-4-methylphenyl)-3-phenyl-1-propanol,
N-(5-nitrosalicyliden)-2-amino-1,1-di(2-butoxy-5-t-butylphenyl )-1-propanol,
N-(5-nitrosalicyliden)-2-amino-1,1-di(2-methoxyphenyl)-3-methyl-1-butanol,
N-(5-nitrosalicylidene)-2-amino-1,1-di-(5-tert-butyl-2-octyoxyphenyl)-1-propanol,
N-(5-nitrosalicylidene)-2-amino-1,1-di(5-tert-butyl-2-tert-butoxyphenyl)-3-phenyl-1-propanol,
N-(3-methoxy-5-nitrosalicyliden)-2-amino-1,1-di(2-butoxy-5-t-butylphenyl )-1-propanol,
N-(3-methoxy-5-nitrosalicyliden)-2-amino-1,1-di(2-methoxyphenyl )-1-propanol,
N-(3-methoxy-5-nitrosalicyliden)-2-amino-1,1-diphenyl-1-propanol,
N-(3-t-butylsalicyliden)-2-amino-1,1-diphenyl-1-propanol,
N-(3,5-di-t-butylsalicyliden)-2-amino-1,1-di(2-methoxyphenyl)-1-propanol, and the like. Said optically active compounds may have either an S configuration or R configuration with respect to the carbon atom denoted by "*" in the formula above.

The salicylidenaminoalcohol of formula (1) is usually contacted with a mono-valent or di-valent copper compound to produce a chiral copper complex in an inert solvent.

Examples of the mono-valent or di-valent copper compound include
 a copper salt of an organic carboxylic acid having 2 to 15 carbon atoms such as copper acetate, copper naphthenate, copper octanoate and the like, and a copper salt such as copper chloride, copper bromide, copper nitrate, copper sulfate, copper methanesulfonte, copper trifluoromethanesulfonate, copper cyanate, copper carbonate and copper oxide, and a mixture thereof.
Examples of the inert solvent include a hydrocarbon such as hexane, heptane, cyclohexane or the like, an ester such as methyl acetate, ethyl acetate, ethyl propionate or the like, a ketone such as acetone, methyl ethyl ketone or the like, a halogenated hydrocarbon such as butyl chloride, dichloroethane, chloroform, carbon tetrachloride or the like, and an aromatic hydrocarbon such as toluene, xylene or the like. The mixture of solvent described above can be also used. An amount thereof to be used is not particularly limited. Prochiral olefins of formula (3) to be used in the next cyclopropanation step may also be used as a solvent.

An amount of the copper compound to be used is less than 1 mole, usually 0.2 to 0.95 mole, preferably 0.4 to 0.94 mole per mol of the optically active salicylideneaminoalcohol compound of formula (1). The reaction temperature is usually room temperature to the boiling point of the solvent used, or typically 10 to 100° C.

The reaction mixture, which is the present chiral copper complex catalyst composition, can be used as it is for the asymmetric synthesis, or it may be concentrated to a suitable concentration, if necessary. The chiral copper catalyst composition thus obtained usually contains 0.1 to 30 (wt) % of the chiral copper complex which is derived from the slicylideneaminoalcohol compound of formula (1) and the copper compound, and the inert solvent. It can also be used after the isolation by removing the solvent.

Alternatively, the resulting reaction mixture may be further contacted-with a base, if necessary.

Examples of the base include
 an alkali metal alcoholate such as sodium methylate and sodium ethylate, which can be used as they are as powders or as a solution in alcohol such as methanol, ethanol or the like,
 alkali metal hydroxide such as sodium hydroxide, potassium hydroxide or the like,
 alkali metal carbonate or bicarbonate such as sodium carbonate, sodium bicarbonate and the like. These are usually used as an aqueous solution.

The amount of the base to be used is usually 0.1–8 moles, preferably around 0.5–3 moles per mole of the copper compound.

Although the resulting reaction mixture can be used as it is without removing a salt produced by neutralization of them (for example, sodium acetate in the case of using copper acetate, sodium naphthenate in the case of using copper naphthenate), it is preferably used after removing the salt by washing with water. In this case, the catalyst may be used after being dehydrated.

Thus obtained chiral copper complex catalyst composition in a solution form, of which concentration is usually within the range of the concentration as described above, optionally adjusted by concentration or addition of an appropriate solvent, can be used in the cyclopropanation reaction, hence a purifying step is not particularly necessary. Although the product can be isolated by removing the solvent, the solution is usually used as it is and, therefore, the present catalyst composition is suitably used in a continuous reaction process because of ready feeding of catalyst.

Although the structure of an asymmetric copper complex catalyst obtained herein is not always clearly established, it shows practically good activity for an industrial production process.

Next, a description will be made to the step of producing optically active cyclopropane-carboxylic acid ester of formula (2) as defined above, which step comprising reacting a prochiral olefin of formula (3) with a diazoacetic acid ester of formula (4) in the presence of a chiral copper complex catalyst composition so produced.

$R_3$, $R_4$, $R_5$ or $R_6$ of the prochiral olefin of formula (3) will be explained below.

Examples of the alkyl group which may be substituted with a halogen atom or an alkoxy group include a linear or branched alkyl group having 1 to 10 carbon atoms such as a methyl, ethyl, n-propyl, isopropyl, n-butyl, isobutyl, sec-butyl, tert-butyl, n-pentyl, n-hexyl, n-heptyl, n-octyl, n-nonyl, or n-decyl group, an alkyl group substituted with a halogen atom such as a fluorine atom, a chlorine atom, a bromine atom and the like a haloalkyl group such as a chloromethyl, dichloromethyl, trichloromethyl, difluoromethyl, trifluoromethyl, 2,2,2-trichloroethyl group or the like, an alkyl group substituted with an alkoxy group such as a methoxy, ethoxy, n-propoxy, i-propoxy group or the like.

Examples of the alkylene group formed by $R_3$ and $R_4$, or $R_5$ and $R_6$ include an alkylene group having 2 to 4 carbon atoms such as dimethylnene, trimethylene, or tetramethylene group.

Examples of the alkenyl group which may be substituted with a halogen atom, an alkoxy group or an alkoxy carbonyl group, of which alkoxy may be substituted with a halogen atom or atoms, represented by $R_3$, $R_4$, $R_5$ include a linear or branched alkenyl groups having 1 to 10 carbon atoms such as an ethenyl, propenyl, 2-methylpropenyl, 1-butenyl, 2-butenyl, or hexenyl group, a haloalkenyl group, which is the above-described alkenyl group substituted with the above-described halogen atom or atoms, such as a chloroethenyl group, a chloropropenyl group, 2,2-dichloroethenyl group, 2,2-difluoroethenyl group or the like, an alkoxy(C1–C3)carbonyl substituted alkenyl group such as 2-methoxycarbonyl-2-methylethenyl group, 2-(1,1,1,3,3,3-hexafluoroisopropoxycarbonyl)-1-methylethenyl group or the like.

Specific examples of the prochiral olefin (3) include propene, 1-butene, isobutylene, 1-pentene, 1-hexene, 1-octene, 4-chloro-1-butene, 2-pentene, 2-heptene, 2-methyl-2-butene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 2-methyl-2,4-hexadiene, 2,3-dimethyl-2-pentene, 1,1,1-trichloro-4-methyl-3-pentene and the like. 1,1-dibromo-4-methyl-1,3-pentadiene, 1-chloro-1-fluoro-4-methyl-1,3-pentadiene, 1-fluoro-1-bromo-4-methyl-1,3-pentadiene, 2-(1,1,1,3,3,3-hexafluoroisopropoxycarbonyl)-5-methyl-2,4-hexadiene, 1-methoxy-4-methyl-1,3-pentadiene, 1-ethoxy-4-methyl-1,3-pentadiene, 1-propoxy-4-methyl-1,3-pentadiene, 1-fluoro-1-methoxy-4-methyl-1,3-pentadiene, 1-fluoro-1-ethoxy-4-methyl-1,3-pentadiene, 1-fluoro-1-propoxy-4-methyl-1,3-pentadiene, 1,1,1-tribromo-4-methyl-3-pentene, 2-bromo-2,2-dimethyl-4-hexene, 2-chloro-2,5-dimethyl-4-hexene, 1-methoxy-2-methyl-1-propene, 1-ethoxy-2-methyl-1-propene, 1-propoxy-2-methyl-1-propene, 1-methoxy-8-methyl-2-butene, 1-ethoxy-3-methyl-2-butene, 1-propoxy-3-methyl-2butene, 1,1-dimethoxy-3-methyl-2-butene, 1,1-diethoxy-3-methyl-2-butene, isopropylidenecyclopropane, isopropylidenecyclobutane, isopropylidenecyclopentane and the like.

Examples of the alkyl group having 1 to 8 carbon atoms represented by $R_7$ in formula (4) include a methyl group, an ethyl group, a n-propyl group, an isopropyl group, a n-butyl group, an isobutyl group, a sec-butyl group, a tert-butyl group, a n-pentyl group, a n-hexyl group, a n-octyl group and the like.

Examples of the cycloalkyl group which may be optionally substituted with a lower alkyl group include a cyclohexyl group, a 1-menthyl group, a d-menthyl group.

Examples of the phenyl or benzyl group which may be optionally substituted with a lower alkyl group, a lower alkoxy group or a phenoxy group represented by $R_7$ in formula (4) include a phenyl group, a 2-methylphenyl group, a 3,5-dimethylphenyl group, a 4-methyl-2,6-di-tert-butylphenyl group, a 2-methoxyphenyl group, a 3,5-dimethoxyphenyl group, a benzyl group, a 3-phenoxybenzyl group and the like.

Examples of the lower alkyl group which may be present on the cycloalkyl group or on the phenyl group include a (C1–C4)alkyl group such as a methyl group, an ethyl group, a n-propyl group, an i-propyl group, a n-butyl group, an i-butyl group, a sec-butyl group, and a t-butyl group.

Examples of the lower alkoxy group which may be present on the phenyl group include a (C1–C4)alkoxyl group such as a methoxy group, an ethoxy group, a n-propoxy group, an i-propoxy group, a n-butoxy group, an i-butoxy group, a sec-butoxy group, and a t-butoxy group.

Preferred are a (C1–C6)alkyl group, a cyclohexyl group, a 1-menthyl group, a d-menthyl group, a phenyl group, a 2-methylphenyl group, a 3,5-dimethylphenyl group, a 4-methyl-2,6-di-tert-butylphenyl group, a 2-methoxyphenyl group, a 3,5-dimethoxyphenyl group and a 3-phenoxybenzyl group.

Specific examples of the diazoacetic acid ester of formula (4) include ethyl diazoacetate, n-propyl diazoacetate, tert-butyl diazoacetate, phenyl diazoacetate, 1-menthyl diazoacetate, cyclohexyl diazoacetate and the like.

Said diazoacetic esters of formula (4) is commercially available or may be prepared by the known method such as a method of reacting corresponding amino acid esters with a diazotizing agent such as sodium nitrite and mineral acids may be used.

The reaction of prochiral olefin of formula (3) with diazoacetic esters of formula (4) in the presence of the prepared copper complex catalyst composition is usually performed by adding the diazoacetic ester of formula (4) to a mixture of the copper complex catalyst composition and the prochiral olefin (3) and optionally in a solvent. The present reaction may be performed in the presence of a reducing agent such as phenylhydrazine or the like.

An amount of prochiral olefins of formula (3) to be used is usually 1 mole or more per mol of the diazoacetic esters of formula (4). The upper limit thereof is not particularly limited and, for example, a large excess amount may be used so as to serve as a reaction solvent.

An amount of the copper complex catalyst to be used is usually 0.001 to 1 mole %, preferably 0.002 to 0.5 mole % in terms of copper relative to diazoacetic esters of formula (4).

Examples of the solvent to be used include a halogenated hydrocarbon such as 1,2-dihloroethane, chloroform, carbon tetrachloride or the like, an aliphatic hydrocarbon such as hexane, heptane, cyclohexane and the like, an aromatic hydrocarbon such as benzene, toluene, xylene and the like, an ester such as methyl acetate, ethyl acetate and the like, and a mixture thereof. Alternatively, prochiral olefin (3) may be used as a solvent.

An amount of the solvent to be used is usually 2 to 50 parts by weight, preferably 3 to 30 parts by weight per 1 part by weight of the diazoacetic ester (4).

A reaction temperature is usually 5 to 150° C., preferably 10 to 120° C. In addition, the reaction is usually performed under an inert gas atmosphere such as a nitrogen gas or the like.

After completion of the reaction, the optically active cyclopropanecarboxylic acid ester derivative of formula (2) can be separated by distillation or the like, which may be subjected to ester hydrolysis or the like, or may be further purified, for example, by distillation, column chromatography or the like, if necessary.

Examples of the optically active cyclopropanecarboxylic acid esters of formula (2) include optically active
methyl 2-methylcyclopropanecarboxylate,
ethyl 2-methylcyclopropanecarboxylate,
n-propyl 2-methylcyclopropanecarboxylate,
isopropyl 2-methylcyclopropanecarboxylate,
isobutyl 2-methylcyclopropanecarboxylate,
tert-butyl 2-methylcyclopropanecarboxylate,
cyclohexyl 2-methylcyclopropanecarboxylate,
menthyl 2-methylcyclopropanecarboxylate,
4-methyl-2,6-di-tert-butylphenyl 2-methylcyclopropanecarboxylate,
methyl 2,2-dimethylcyclopropanecarboxylate,
ethyl 2,2-dimethylcyclopropanecarboxylate,
n-propyl 2,2-dimethylcyclopropanecarboxylate,
isopropyl 2,2-dimethylcyclopropanecarboxylate,
isobutyl 2,2-dimethylcyclopropanecarboxylate,
tert-butyl 2,2-dimethylcyclopropanecarboxylate,
cyclohexyl, 2,2-dimethylcyclopropanecarboxylate,
menthyl 2,2-dimethylcyclopropanecarboxylate,
methyl 2,2,3-trimethylcyclopropanecarboxylate,
ethyl 2,2,3-trimethylcyclopropanecarboxylate,
n-propyl 2,2,3-trimethylcyclopropanecarboxylate,
isopropyl 2,2,3-trimethylcyclopropanecarboxylate,
isobutyl 2,2,3-trimethylcyclopropanecarboxylate,
tert-butyl 2,2,3-trimethylcyclopropanecarboxylate,
cyclohexyl, 2,2,3-trimethylcyclopropanecarboxylate,
menthyl 2,2,3-trimethylcyclopropanecarboxylate,
4-methyl-2,6-di-tert-butylphenyl 2,2-dimethylcyclopropanecarboxylate,
methyl 2,2-dimethyl-3-(2-methyl-1-propenyl) cyclopropanecarboxylate,
ethyl 2,2-dimethyl-3-(2-methyl-1-propenyl) cyclopropanecarboxylate,
n-propyl 2,2-dimethyl-3-(2-methyl-1-propenyl) cyclopropanecarboxylate,
isopropyl 2,2-dimethyl-3-(2-methyl-1-propenyl) cyclopropanecarboxylate,
isobutyl 2,2-dimethyl-3-(3-methyl-1-propenyl) cyclopropanecarboxylate,
tert-butyl 2,2-dimethyl-3-(2-methyl-1-propenyl) cyclopropanecarboxylate,
cyclohexyl 2,2-dimethyl-3-(2-methyl-1-propenyl) cyclopropanecarboxylate,
menthyl 2,2-dimethyl-3-(2-methyl-1-propenyl) cyclopropanecarboxylate,
(4-methyl-2,6-di-tert-butylphenyl) 2,2-dimethyl-3-(2-methyl-1-propenyl) cyclopropanecarboxylate,
methyl 2,2-dimethyl-3-(2,2-dichloro-1-ethenyl) cyclopropanecarboxylate,
ethyl 2,2-dimethyl-3-(2,2-dichloro-1-ethenyl) cyclopropanecarboxylate,
n-propyl 2,2-dimethyl-3-(2,2-dichloro-1-ethenyl) cyclopropanecarboxylate,
isopropyl 2,2-dimethyl-3-(2,2-dichloro-1-ethenyl) cyclopropanecarboxylate,
isobutyl 2,2-dimethyl-3-(2,2-dichloro-1-ethenyl) cyclopropanecarboxylate,
tert-butyl 2,2-dimethyl-3-(2,2-dichloro-1-ethenyl) cyclopropanecarboxylate,
cyclohexyl 2,2-dimethyl-3-(2,2-dichloro-1-ethenyl) cyclopropanecarboxylate,
menthyl 2,2-dimethyl-3-(2,2-dichloro-1-ethenyl) cyclopropanecarboxylate,
(4-methyl-2,6-di-tert-butylphenyl) 2,2-dimethyl-3-(2,2-dichloro-1-ethenyl)cyclopropanecarboxylate,
methyl 2,2-dimethyl-3-(2,2,2-trichloroethyl) cyclopropanecarboxylate,
ethyl 2,2-dimethyl-3-(2,2,2-trichloroethyl) cyclopropanecarboxylate,
n-propyl 2,2-dimethyl-3-(2,2,2-trichloroethyl) cyclopropanecarboxylate,
isopropyl 2,2-dimethyl-3-(2,2,2-trichloroethyl) cyclopropanecarboxylate,
isobutyl 2,2-dimethyl-3-(2,2,2-trichloroethyl) cyclopropanecarboxylate,
tert-butyl 2,2-dimethyl-3-(2,2,2-trichloroethyl) cyclopropanecarboxylate,
cyclohexyl 2,2-dimethyl-3-(2,2,2-trichloroethyl) cyclopropanecarboxylate,
menthyl 2,2-dimethyl-3-(2,2,2-trichloroethyl) cyclopropanecarboxylate,
4-methyl-2,6-di-tert-butylphenyl 2,2-dimethyl-3-(2,2,2-trichloroethyl) cyclopropanecarboxylate and the like.

The optically active salicylideneaminoalcohol compound of formula (1) contained in the residue after isolating the optically active cyclopropanecarboxylic acid ester derivative of formula (2) can be recovered by subjecting the residue to crystallization treatment, column chromatography or the like.

The optically active salicylideneaminoalcohol compound of formula (1) can be obtained, for example, by reacting an optically active amino alcohol of formula (5):

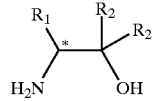

(5)

wherein $R_1$ and $R_2$ have the same meaning s as defined above, with a salicylaldehyde derivative of formula (6):

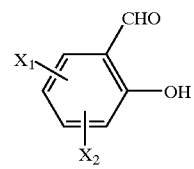

(6)

wherein $X_1$ and $X_2$ are the same as defined above.

The optically active amino alcohol compound of formula (5) to be used in this process include those having $R_1$ and $R_2$ groups as specified above and specific examples thereof include optically active
2-amino-1,1-diphenyl-1-propanol,
2-amino-1,1-di(2-methoxyphenyl)-1-propanol,
2-amino-1,1-di(2-isopropoxyphenyl)-1-propanol,
2-amino-1,1-di(2-butoxy-5-t-butylphenyl)-1-propanol,
2-amino-1,1-diphenyl-3-phenyl-1-propanol,
2-amino-1,1-di(2-methoxyphenyl)-3-phenyl-1-propanol,
2-amino-1,1-di(2-isopropoxyphenyl)-3-phenyl-1-propanol,
2-amino-1,1-di(2-butoxy-5-t-butylphenyl)-3-phenyl-1-propanol, 2-amino-1,1-di(2-methoxyphenyl)-3-phenyl-1-butanol,
2-amino-1,1-di(2-butoxy-5-t-butylphenyl)-1-propanol,
2-amino-1,1-di(2-octyloxy-5-t-butylphenyl)- -propanol,
2-amino-1,1-di(2-butoxy-5-t-butylphenyl)-3-phenyl-1-propanol,
2-amino-1,1-di(2-methoxyphenyl)-1-propanol,
2-amino-1,1-di(2-benzyloxy-5-methylphenyl)-3-(4-isopropoxyphenyl)-1-propanol,
2-amino-1,1-di(2-methoxyphenyl)-3-methyl-1-butanol,
2-amino-3-phenyl-1-propanol,
2-amino-1,1-di(2-t-butyl-4-methylphenyl)-3-phenyl-1-propanol,
2-amino-1,1-di(4-t-butylphenyl)-1-propanol,
2-amino-1,1-di(2-methoxyphenyl)-3-methyl-1-propanol and the like.

The reaction of the optically active amino alcohol (5) with the salicylaldehyde derivative (6) is usually conducted at room temperature to the boiling point of the solvent used.

Said reaction is usually conducted by contacting the optically active amino alcohol (5) with the slicylaldehyde derivative (6) in an organic solvent, examples of which include an aromatic hydrocarbon solvent such as toluene, xylene or the like, a halogenated hydrocarbon solvent such as chlorobenzene, dichloroethane or the like and an alcohol solvent such as methanol, ethanol or the like and a mixture thereof An amount thereof to be used is not particularly limited.

An amount of the slicylaldehyde derivative to be used is usually 0.8 to 1.5 moles, preferably 0.9 to 1.2 moles per mol of the optically active amino alcohol of formula (5). The reaction may be conducted under dehydrating water which is produced during the reaction.

EXAMPLES

The present invention will be illustrated by way of the following Examples but are not to be construed to limit the present invention thereto.

The yield and the optical purity were calculated according to the following equations.

Yield (%)=$B \times 100/A$ optical purity of obtained cyclopropanecarboxylate:

(+)-trans e.e. %=$(C-D) \times 100/(C+D)$ (+)-cis e.e. %=$(E-F) \times 100/(E+F)$ provided that,
A=employed diazoacetic ester (mol)
B=cyclopropanecarboxylic ester (mol) produced after the reaction
C=(+)-trans-isomer
D=(−)-trans-isomer
E=(+)-cis-isomer
F=(−)-cis-isomer

Reference Example 1

0.968 g (2.0 mmol) of (R)-2-amino-1,1-di(2-butoxy-5-t-butylphenyl)-propanol and 0.244 g (2.0 mmol) of salicylaldehyde were dissolved in 20 ml of ethanol and 20 ml of toluene, the solution was heated at reflux for 1 hour. The solvent was distilled off from the reaction mixture and dried to obtain 1.17 g of (R)-N-salicyliden-2-amino-1,1-di(2-butoxy-5-t-butylphenyl)-propanol as a yellow solid.

Example 1

After a glass Schlenk tube having an inner volume of 50 ml was purged with nitrogen, 58.8 mg(0.1 mmol) of (R)-N-salicyliden-2-amino-1,1-di(2-butoxy-5-t-butylphenyl)-propanol obtained in Reference Example 1 and a 5% solution of 63.5 mg(containing 0.05 mg-atom Cu) of copper naphthenate in toluene were dissolved in 25 ml of dry toluene at room temperature for 1 hour, 19.3 mg of 28% sodium methylate in methanol was added, and the mixture was stirred at room temperature for 1 hour to prepare a complex catalyst solution.

A stirrer was placed in a Schlenk tube having an inner volume of 100 ml, the tube was purged with a nitrogen gas, and 5 ml (Cu 0.01 mg-atom) of the complex catalyst prepared above was added therein. Next, after 30 g (273 mmol) of 2,5-dimethyl-2,4-hexadiene was added, 1.1 mg (0.01 mmol) of phenylhydrazine was added. Thereafter, the Schlenk tube was warmed to 80° C., and 10 ml of a solution of ethyl diazoacetate in toluene (containing ethyl diazoacetate:20 mmol) was added thereto over 2 hours. After the addition, the mixture was kept at 80° C. for 30 minutes, cooled to a room temperature and the yield of the product of chrysanthemic acid ester and the isomer ratio of trans/cis were analyzed by Gas chromatography, and the optical purity was analyzed by high-performance liquid chromatography. The yield of chrysanthemic acid ethyl ester was 90.1% based on ethyl diazoacetate employed, trans/cis was 55/45, and optical purity was 71% e.e.(trans) and 60% e.e.(cis).

Examples 2 to 16

Optically active Salicylideneaminoalcohol compounds were synthesized from optically active aminoalcohols and salicylaldehyde derivatives as in Reference Example 1. The results are summarized in Table 1, and the complex catalyst solutions were prepared using optically active salicylideneaminoalcohol compound, copper naphthenate and sodium methylate as shown in Table 1.

The cyclopropanation reaction was performed using the chiral copper complex catalyst compositions shown in Table 2 as in Example 1.

Example 17

Optically active Salicylideneaminoalcohol compound were synthesized from optically active aminoalcohols and salicylaldehyde derivatives as in Reference Example 1 To a 100 ml Schlenk, 0.2 mmol of (R)-N-(5-nitrosalicylidene)-2-amino-1,1-di(2-butoxy-5-t-butylphenyl)-1-propanol were added 35.9 mg(0.18 mmol) of copper acetate monohydrate and 50 ml of toluene, and the resulting mixture was reacted for 1 hour under stirring at 80° C. The reaction mixture was cooled to a room temperature, and an aqueous solution of 40 mg of sodium hydroxide dissolved in 30 ml of water was added thereto. The mixture was transferred to a separatory funnel, and was thoroughly stirred, settled and the separated aqueous layer was removed. 10 ml of water was added thereto, stirred again and settled. The oily layer was transferred to a Schlenk tube and azeotropically dehydrated under heating to give the product. The product was diluted with toluene to make a 50 ml toluene solution of the optically active copper complex catalyst mixture.

To a 100 ml Schlenk tube purged with nitrogen were added 1 ml of the optically active copper complex catalyst solution prepared above and the same starting material as used in Example 1, and the resulting mixture was reacted according to the same manner as in Example 1. The results are shown in Table 2.

Example 18

A chiral copper complex was prepared according to the similar manner as in Example 17 except that the salicylideneaminoalcohol compound obtained in Example 6 were used. Ethyl cyclopropanecarboxylate derivative was produced with the chiral copper complex. The results are shown in Table 2.

Example 19

10 ml (Cu 0.02 mg-atom) of the copper complex catalyst solution prepared in Example 1 was added to an stainless autoclave with 100 ml-volume purged with nitrogen gas beforehand. 2.2 mg (0.02 mmol )of phenylhydrazine and 4.5 g (80.4 mmol) of isobutylene were added thereto. Then the reaction mixture was heated to 40 ° C., and 10 ml of ethyl diazoacetate (20 mmol) in toluene were added thereto over 2 hrs with a pump. Thereafter the reaction mixture was kept at 40° C. for 1 hours, and then cooled to a room temperature. Yield of the ethyl cyclopropane-carboxylate was analyzed by gaschoromatography. The optical purity of the product was determined by derivatizing the product to 1-menthylate ester thereof. Yield 91% (vs. ethyl diazoacetate), Optical purity: 81% e.e.

Example 20

Ethyl cyclopropane-carboxylate derivative was produced according to a similar manner as in Example 19 except that 10 ml of the copper complex catalyst prepared in Example 4. The results are shown in Table 2.

Example 21

Ethyl cyclopropane-carboxylate derivative was produced according to a similar manner as in Example 19 except that 10 ml of the copper complex catalyst prepared in Example 5. The results are shown in Table 2.

Example 22

To a 100 ml Schlenk tube, were added 0.2 mmol of (R)-N-salicylidene-2-amino-1,1-di(2-butoxy-5-t-butylphenyl)-1-propanol, 35.9 mg(0.18 mmol) of copper acetate monohydrate and 50 ml of toluene, and the resulting mixture was reacted for 1 hour under stirring at 80° C. The reaction mixture was cooled to a room temperature, and an aqueous solution of 40 mg of sodium hydroxide dissolved in 30 ml of distilled water was added thereto. The mixture was transferred to a separatory funnel, and was thoroughly stirred, settled and the separated aqueous layer was removed. 10 ml of distilled water was added thereto and stirred again. After settled, the oily layer was transferred to a Schlenk tube, a condensing tube equipped with a separatory tube amounted thereon, the reaction solution was azeotropically dehydrated under heating to give the catalyst composition. Toluene was added to make a 50 ml toluene solution of the optically active copper complex catalyst. Ethyl cyclopropanecarboxylate derivative was produced according to a similar manner as in Example 19 except that 10 ml of the copper complex catalyst prepared above was used . The results are shown in Table 2.

Example 23

Ethyl cyclopropane-carboxylate derivative was produced according to a similar manner as in Example 19 except that 2.5 ml of the copper complex catalyst solution prepared in Example 2 were used. Yield: 91% (based on the ethyl diazoacetate), Optical purity: 86% e.e.

Example 24

Ethyl cyclopropane-carboxylate derivative was produced according to a similar manner as in Example 19 except that 2.5 ml of the copper complex catalyst prepared in Example 12 were used. Yield: 92%, Optical Purity: 87% e.e.

Example 25

An optically active Salicylideneaminoalcohol compound were synthesized from optically active aminoalcohols and salicylaldehyde derivatives as in Example 2.

After a glass Schlenk tube having an inner volume of 50 ml was purged with nitrogen, 16.4 mg(0.0259 mmol) of (R)-N-(5-nitorosalicyliden)-2-amino-1,1-di(2-butoxy-5-t-butylphenyl)-1-propanol obtained in Example 2 and a 5% solution of 29.8mg(containing 0.0235 mg-atom Cu) of copper naphthenate in toluene were dissolved in 13 ml of dry ethyl acetate saturated with a nitrogen gas at room temperature for 1 hour to prepare a complex catalyst solution.

Ethyl cyclopropane-carboxylate derivative was produced according to a similar manner as in Example 1 except that 4 ml of the copper complex catalyst solution prepared were used. The yield of chrysanthemic acid ethyl ester was 89.2% relative to employed ethyl diazoacetate, trans/cis was 54/46, and optical purity was 66% e.e.(trans) and 46% e.e.(cis).

Example 26

A chiral copper complex prepared according to the similar manner as in Example 25 except that the (R)-N-(5-nitorosalicyliden)-2-amino-1,1-di(2-methoxyphenyl)-1-propanol was used in place of (R)-N-(5-nitorosalicyliden)-2-amino-1,1-di(2-butoxy-5-t-butylphenyl)-1-propanol.

Ethyl cyclopropane-carboxylate derivative was produced according to a similar manner as in Example 1. The yield of chrysanthemic acid ethyl ester was 90.9% relative to employed ethyl diazoacetate, trans/cis was 59/41, and optical purity was 55% e.e.(trans) and 47% e.e.(cis).

TABLE 1

Optically active salicylideneaminoalcohol compounds (1).

| Ex. | Optically active aminoalcohol compound (5) | Salicylaldehyde derivative (6) | Optically active salicylideneaminoalcohol compound (1) | (Copper complex composition) optical rotation $\alpha_D$ (20° c., 1 cm) |
|---|---|---|---|---|
| 1 | (R)-2-amino-1,1-di(2-butoxy-5-t-butylphenyl)-1-propanol 0.968 g (2.0 mml) | salicylaldehyde 0.244 g (2.0 mmol) | (R)-N-salicyliden-2-amino-1,1-di(2-butoxy-5-t-butylphenyl)-1-propanol, 58.8 mg (0.1 mmol) | |

TABLE 1-continued

Optically active salicylideneaminoalcohol compounds (1).

| Ex. | Optically active aminoalcohol compound (5) | Salicylaldehyde derivative (6) | Optically active salicylideneaminoalcohol compound (1) | (Copper complex composition) optical rotation $\alpha_D$ (20° c., 1 cm) |
|---|---|---|---|---|
| 2 | (R)-2-amino-1,1-di(2-butoxy-5-t-butylphenyl)-1-propanol 0.968 g (2.0 mmol) | 2-hydroxy-5-nitro-benzaldehyde 0.334 g (2.0 mmol) | (R)-N-(5-nitrosalicylidene)-2-amino-1,1-di(2-butoxy-5-t-butylphenyl)-1-propanol 63.3 mg (0.1 mmol) | +0.113° |
| 3 | (R)-2-amino-1,1-di(2-butoxy-5-t-butylphenyl)-1-propanol 0.968 g (2.0 mmol) | 2-hydroxy-3-fluoro-benzaldehyde 0.244 g (2.0 mmol) | (R)-N-(3-fluorosalicylidene)-2-amino-1,1-di(2-butoxy-5-t-butylphenyl)-1-propanol 60.6 mg (0.1 mmol) | +0.068° |
| 4 | (R)-2-amino-1,1-di(2-methoxy-phenyl)-1-propanol 0.575 g (2.0 mmol) | salicylaldehyde 0.244 g (2.0 mmol) | (R)-N-salicylidene-2-amino-1,1-di(2-methoxyphenyl)-1-propanol 39.1 mg (0.1 mmol) | |
| 5 | (R)-2-amino-1,1-diphenyl-1-propanol 0.455 g (2.0 mmol) | salicylaldehyde 0.244 g (2.0 mmol) | (R)-N-salicyliden-2-amino-1,1-diphenyl-1-propanol 33.1 mg (0.1 mmol) | |
| 6 | (R)-2-amino-1,1-diphenyl-1-propanol 0.455 g (2.0 mmol) | 2-hydroxy-5-nitro-benzaldehyde 0.334 g (2.0 mmol) | (R)-N-(5-nitrosalicylidene)-2-amino-1,1-diphenyl-1-propanol 37.6 mg (0.1 mmol) | |
| 7 | (R)-2-amino-1,1-diphenyl-1-propanol 0.455 g (2.0 mmol) | 2-hydroxy-3-fluoro-benzaldehyde 0.28 g (2.0 mmol) | (R)-N-(3-fluorosalicylidene)-2-amino-1,1-diphenyl-1-propanol 34.9 mg (0.1 mmol) | −0.208° |
| 8 | (R)-2-amino-1,1-diphenyl-1-propanol 0.455 g (2.0 mmol) | 2-hydroxy-5-bromo-benzaldehyde 0.402 g (2.0 mmol) | (R)-N-(5-bromosalicylidene)-2-amino-1,1-diphenyl-1-propanol 41.0 mg (0.1 mmol) | |
| 9 | (R)-2-amino-1,1-diphenyl-1-propanol 0.455 g (2.0 mmol) | 2-hydroxy-3,5-di-bromobenzaldehyde 0.56 g (2.0 mmol) | (R)-N-(3,5-dibromosalicylidene)-2-amino-1,1-diphenyl-1-propanol, 48.9 mg (0.1 mmol) | |
| 10 | (S)-2-amino-1,1-di(2-benzyloxy-5-methyl-phenyl)-3-(3-isopropoxy-phenyl)-1-propanol 1.2 g (2.0 mmol) | 2-hydroxy-5-nitro-benzaldehyde 0.334 g (2.0 mmol) | (S)-N-(5-nitrosalicylidene)-2-amino-1,1-di(2-benzyloxy-5-methylphenyl)-3-(4-isopropoxyphenyl)-1-propanol 74.8 mg (0.1 mmol) | −0.143° |
| 11 | (S)-2-amino-1,1-di(2-benzyloxy-5-methyl-phenyl)-3-(3-isopropoxy-phenyl)-1-propanol 1.2 g (2.0 mmol) | 2-hydroxy-3-fluoro-benzaldehyde 0.28 g (2.0 mmol) | (S)-N-(3-fluorosalicylidene)-2-amino-1,1-di(2-benzyloxy-5-methylphenyl)-3-(4-isopropoxyphenyl)-1-propanol 72.1 mg (0.1 mmol) | −0.156° |
| 12 | (R)-2-amino-1,1-di(2-butoxy-5-t-butylphenyl)-3-phenyl-1-propanol 1.12 g (2.0 mmol) | 2-hydroxy-5-nitro-benzaldehyde 0.334 g (2.0 mmol) | (S)-N-(5-nitrosalicylidene)-2-amino-1,1-di(2-butoxy-5-t-butylphenyl)-3-phenyl-1-propanol, 70.9 mg (0.1 mmol) | +0.106° |
| 13 | (R)-2-amino-1,1-di(2-butoxy-5-t-butylphenyl)-3-phenyl-1-propanol 1.12 g (2.0 mmol) | 2-hydroxy-3-fluoro-benzaldehyde 0.28 g (2.0 mmol) | (S)-N-(3-fluorosalicylidene)-2-amino-1,1-di(2-butoxy-5-t-butylphenyl)-3-phenyl-1-propanol, 68.9 mg (0.1 mmol) | +0.13° |
| 14 | (R)-2-amino-1,1-diphenyl-3-phenyl-1-propanol 0.607 g (2.0 mmol) | 2-hydroxy-5-nitro-benzaldehyde 0.334 g (2.0 mmol) | (R)-N-(5-nitrosalicylidene)-2-amino-1,1-diphenyl-3-phenyl-1-propanol, 45.2 mg (0.1 mmol) | +0.039° |
| 15 | (R)-2-amino-1,1-diphenyl-3-phenyl-1-propanol 0.607 g (2.0 mmol) | 2-hydroxy-3-fluoro-benzaldehyde 0.28 g (2.0 mmol) | (R)-N-(3-fluorosalicylidene)-2-amino-1,1-diphenyl-3-phenyl-1-propanol, 42.5 mg (0.1 mmol) | +0.085° |
| 16 | (S)-2-amino-1,1-di(2-methoxyphenyl)-3-methyl-1-butanol 0.632 g (2.0 mmol) | 2-hydroxy-5-nitro-benzaldehyde 0.334 g (2.0 mmol) | (R)-N-(5-nitrosalicylidene)-2-amino-1,1-di(2-methoxy-phenyl)-3-methyl-butanol, 46.5 mg (0.1 mmol) | |
| 17 | (S)-2-amino-1,1-di(2-methoxyphenyl)-3-methyl-1-butanol 0.632 g (2.0 mmol) | 2-hydroxy-3-fluoro-benzaldehyde 0.28 g (2.0 mmol) | (R)-N-(3-fluorosalicylidene)-2-amino-1,1-di(2-methoxy-phenyl)-3-methyl-butanol, 43.8 mg (0.1 mmol) | −0.239° |
| 18 | (R)-2-amino-1,1-di-phenyl-1-1-propanol 0.455 g (2.0 mmol) | 2-hydroxy-3,5-dinitro-benzaldehyde 0.358 g (2.0 mmol) | (R)-N-(3,5-dinitrosalicylidene)-2-amino-1,1-diphenyl-1-propanol | |

TABLE 1-continued

Optically active salicylideneaminoalcohol compounds (1).

| Ex. | Optically active aminoalcohol compound (5) | Salicylaldehyde derivative (6) | Optically active salicylideneaminoalcohol compound (1) | (Copper complex composition) optical rotation $\alpha_D$ (20° c., 1 cm) |
|---|---|---|---|---|
| 19 | (R)-2-amino-1,1-di-phenyl-1-propanol 0.455 g (2.0 mmol) | 2-hydroxy-3-methoxy-5-nitrobenzaldehyde 0.328 g (2.0 mmol) | (R)-N-(3-methoxy-5-dinitro-salicylidene)-2-amino-1,1-diphenyl-1-propanol | |

Properties of n-salicylideneaminoalcohols obtained by examples are shown below. m.p. measured by automatical melting point measuring apparatus manufactured by Metler ®. δ Values of $^1$H-NMR (CDCl$_3$, TMS) are given below.

2: (R)-N-(5-nitrosalicylidene)-2-amino-1,1-di(2-butoxy-5-t-butylphenyl)-1-propanol
δ: 0.87–1.56(m, 35H), 3.72–3.81(m, 4H), 5.08(s, 1H), 5.5(s, 1H), 6.63–8.05(m, 11H). m.p. 67.9° c.
3: (R)-N-(3-florosalicylidene)-2-amino-1,1-di(2-butoxy-5-t-butylphenyl)-1-propanol
δ: 0.86–1.57(m, 35H), 3.66–3.77(m, 4H), 4.95(s, 1H), 5.34(s, 1H), 6.4–8.01(m, 11H). m.p. 51.9° c.
6: (R)-N-(5-nitrosalicylidene)-2-amino-1,1-diphenyl-1-propanol
δ: 1.34–1.36(d, 3H), 2.59(s, 1H), 4.64–4.66(q, 1H), 6.82–6.9(m, 1H), 7.2–7.54(m, 11H), 8.12–8.15(m, 2h), 8.26 (s, 1h) m.p. 208.3° c.
7: (R)-N-(3-fluorosalicylidene)-2-amino-1,1-diphenyl-1-propanol
δ: 1.27–1.29(d, 3H), 2.58(s, 1H), 4.54–4.61(q, 1H), 6.7–7.54(m, 14H), 8.34(s, 1H). m.p. 100° c.
8: (R)-N-(3-bromosalicylidene)-2-amino-1,1-diphenyl-1-propanol
δ: 1.25–1.27(d, 3H), 2.56(s, 1H), 4.55–4.62(q, 1H), 6.76–6.91(d, 1H), 7.15–7.54(m, 13H), 8.28(s, 1H). m.p. 173° c.
9: (R)-N-(3,5-dibromosalicylidene)-2-amino-1,1-diphenyl-1-propanol
δ: 1.28–1.30(d, 3H), 2.59(s, 1H), 4.52–4.59(q, 1H), 7.1–7.66(m, 13H), 8.13(s, 1H). m.p. 128.1° c.
10: (S)-N-(5-nitrosalicylidene)-2-amino-1,1-di(2-benzyloxy-5-methylphenyl)-3-(4-isopropoxyphenyl)-1-propanol
δ: 1.26–1.31(q, 6H), 1.94(s, 3H), 2.13(s, 3H), 2.87–2.91(d, 2H), 4.42–4.50(m, 1H), 4.82–4.95(m, 4H), 5.86(s, 1H), 6.59–8.02(m, 26H)
11: (S)-N-(3-fluorosalicylidene)2-amino-1,1-di(2-benzyloxy-5-methylphenyl)-3-(4-isopropoxyphenyl)-1-propanol
δ: 1.27–1.31(t, 6H), 1.94(s, 3H), 2.11(s, 3H), 2.91–2.94(m, 2H), 4.42–4.50(m, 1H), 4.77–4.92(m, 4H), 5.67(s, 1H), 6.31–7.39(m, 26H). m.p. 82.7° c.
12: (R)-N-(5-nitrosalicylidene)-2-amino-1,1-di(2-butoxy-5-t-butylphenyl)-3-phenyl-1-propanol
δ: 0.91–1.57(m, 34H), 3.78–3.96(m, 4H), 5.05(s, 1H), 5.75(s, 1H), 6.62–8.57(m, 16H). oil
13: (R)-N-(3-fluorosalicylidene)-2-amino-1,1-di(2-butoxy-5-t-butylphenyl)-3-phenyl-1-propanol
δ: 0.87–1.56(m, 34H), 3.71–3.97(m, 4H), 4.85(s, 1H), 5.75(s, 1H), 6.62–8.57(m, 16H). oil
14: (R)-N-(5-nitrosalicylidene)-2-amino-1,1-diphenyl-3-phenyl-1-propanol. m.p. 202° c.
15a: (R)-N-(3-fluorosalicylidene)-2-amino-1,1-diphenyl-3-phenyl-1-propanol m.p. 159.8° c.
16: (S)-N-(5-nitrosalicylidene)-2-amino-1,1-di(2-methoxyphenyl)-3-methyl-1-butanol m.p. 118.7° c.
17: (S)-N-(3-fluorocalicylidene)-2-amino-1,1-di(2-methoxyphenyl)-3-methyl-1-butanol m.p. 79.6° c.

TABLE 2

Results of cyclopropanation reaction

| Ex. | Amount of Chiral copper complex ml*[1] (mg-atom Cu) | Cu mol % vs. Ethyl diazo-acetate | Yield*[2] (%) Cyclopropane-carboxylate (2) | t/c ratio | t % e.e. | c % e.e. |
|---|---|---|---|---|---|---|
| 1 | 5 ml (0.01) | 0.05 | 90 | 55/45 | 71 | 60 |
| 2 | 2.5 ml (0.005) | 0.025 | 92 | 54/46 | 74 | 49 |
| 3 | 2.5 ml (0.005) | 0.025 | 90 | 55/45 | 76 | 58 |
| 4 | 5 ml (0.01) | 0.05 | 92 | 59/41 | 59 | 59 |
| 5 | 5 ml (0.01) | 0.05 | 92 | 60/40 | 52 | 50 |
| 6 | 2.5 ml (0.005) | 0.025 | 93 | 61/39 | 53 | 46 |
| 7 | 2.5 ml (0.005) | 0.025 | 93 | 61/39 | 48 | 46 |
| 8 | 2.5 ml (0.005) | 0.025 | 92 | 61/39 | 48 | 46 |
| 9 | 2.5 ml (0.005) | 0.025 | 93 | 62/38 | 49 | 45 |
| 10 | 1.0 ml (0.002) | 0.01 | 88 | 56/44 | −70 | −55 |
| 11 | 1.0 ml (0.002) | 0.01 | 87 | 58/42 | −69 | −60 |
| 12 | 2.5 ml (0.005) | 0.025 | 90 | 55/45 | 74 | 40 |
| 13 | 2.5 ml (0.005) | 0.025 | 91 | 57/43 | 77 | 49 |
| 14 | 2.5 ml (0.005) | 0.025 | 90 | 62/38 | 62 | 47 |
| 15 | 2.5 ml (0.005) | 0.025 | 93 | 62/38 | 54 | 44 |
| 16 | 2.5 ml (0.005) | 0.025 | 93 | 59/41 | −64 | −55 |
| 17 | 1 ml (0.0036) | 0.018 | 91 | 54/46 | 70 | 48 |
| 18 | 1 ml (0.0036) | 0.018 | 95 | 61/39 | 53 | 49 |
| 19 | 10 ml (0.02) | 0.1 | 91 | | 81 | |
| 20 | 10 ml (0.02) | 0.1 | 81 | | 69 | |
| 21 | 10 ml (0.02) | 0.1 | 79 | | 65 | |
| 22 | 10 ml (0.036) | 0.18 | 91 | | 87 | |
| 23 | 2.5 ml (0.005) | 0.025 | 91 | | 86 | |
| 24 | 2.5 ml (0.005) | 0.025 | 92 | | 87 | |

*[1]Employed amount of a chiral copper complex catalyst solution.
*[2]Based on the diazoacetic acid ester.

What is claimed is:
1. A chiral copper complex catalyst composition, which is obtained by contacting an optically active N-salicylideneaminoalcohol compound of formula (1):

(1)

with a mono-valent or di-valent copper compound in an inert solvent, wherein $R_1$ represents an alkyl group which may be substituted with a group selected from an alkoxy group, an aralkyloxy group, an aryloxy group and a cycloalkoxy group, an aralkyl, aryl or cycloalkyl group all of which may be substituted with a group selected from an alkyl group, an alkoxy group, an aralkyloxy group, an aryloxy group, and a cycloalkoxy group, $R_2$ represents a hydrogen atom, an alkyl group, a cycloalkyl group, or an aralkyl or phenyl group which may be substituted with a group selected from an alkyl group, an alkoxy group, an aralkyloxy group, an aryloxy group and a cycloalkoxy group, $X_1$ and $X_2$ are the same or different and independently represent a hydrogen atom, a halogen atom, a nitro group, an alkyl group, an alkoxy group or a cyano group, and two adjacent $X_1$ and $X_2$ together with the benzene ring to which they are bonded may form a 1-hydroxy-2- or 2-hydroxy-1-naphthyl group, and the carbon atom denoted by "*" is an asymmetric carbon atom having either an S or R configuration, and the amount of the mono-valent or di-valent copper compound is less than 1 mole per 1 mole of the optically active N-salicylideneaminoalcohol compound of formula (1).

2. A process for producing an optically active cyclopropane-carboxylic acid ester of formula (2):

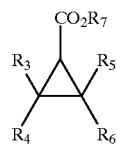

(2)

wherein $R_3$, $R_4$, $R_5$ and $R_6$ are as defined below, and $R_7$ represents an alkyl group having 1 to 8 carbon atoms, a cycloalkyl group which may be optionally substituted with a lower alkyl group, a benzyl group or phenyl group which may be optionally substituted with a lower alkyl group, a lower alkoxy group or a phenoxy group, which comprises the steps of:

(a) contacting an optically active N-salicylideneaminoalcohol compound of formula (1):

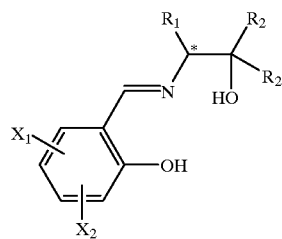

(1)

with a mono-valent or di-valent copper compound, in an inert solvent, wherein $R_1$ represents an alkyl group which may be substituted with a group selected from an alkoxy group, an aralkyloxy group, an aryloxy group, and a cycloalkoxy group, an aralkyl, aryl or cycloalkyl group all of which may be substituted with a group selected from an alkyl group, an alkoxy group, an aralkyloxy group, an aryloxy group, and a cycloalkoxy group, $R_2$ represents a hydrogen atom, an alkyl group, a cycloalkyl group, or an aralkyl or phenyl group which may be substituted with a group selected from an alkyl group, an alkoxy group, an aralkyloxy group, an aryloxy group, and a cycloalkoxy group, $X_1$ and $X_2$ are the same or different and independently represent a hydrogen atom, a halogen atom, a nitro group, an alkyl group, an alkoxy group or a cyano group, and two adjacent $X_1$ and $X_2$ together with the benzene ring to which they are bonded may form a 1-hydroxy-2- or 2-hydroxy-1-naphthyl group, and the carbon atom denoted by "*" is an asymmetric carbon atom having either an S or R configuration, and the amount of the mono-valent or di-valent copper compound is less than 1 mole per 1 mole of the optically active N-salicylideneaminoalcohol compound of formula (1), and (b) reacting a prochiral olefin of formula (3):

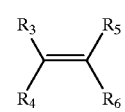

(3)

wherein $R_3$, $R_4$, $R_5$ and $R_6$ independently represent a hydrogen atom, a halogen atom, a (C1–C10)alkyl group which may be substituted with a halogen atom or a lower alkoxy group, a (C4–C8)cycloalkyl group, an aryl group which may be substituted with a halogen atom, a lower alkyl group or a lower alkoxy group, $R_3$ and $R_4$, or $R_5$ and $R_6$ may be bonded at their terminals to form an alkylene group having 2–4 carbon atoms, and one of $R_3$, $R_4$, $R_5$ and $R_6$ groups represents an alkenyl group which may be substituted with a halogen atom, an alkoxy group or an alkoxy carbonyl group, of which alkoxy may be substituted with a halogen atom or atoms, provided that when $R_3$ and $R_5$ are the same, $R_4$ and $R_6$ are not the same, with a diazoacetic acid ester of formula (4):

$$N_2CHCO_2R_7 \quad (4)$$

wherein $R_7$ is the same as defined above, in the presence of a chiral copper complex catalyst composition so produced in step (a) without being isolated.

3. The chiral copper complex catalyst composition according to claim 1, which is obtained by contacting an optically active N-salicylideneaminoalcohol compound of formula (1) as defined in claim 1 with a mono-valent or di-valent copper compound in an inert solvent, contacting the resulting mixture with a base, and optionally washing the resulting mixture with water and dehydrating.

4. The chiral copper complex catalyst composition according to claim 1 or 3, wherein $R_1$ represents an (C1–C8)alkyl group which may be substituted with a group selected from an (C1–C4)alkoxy group, an (C7–C11)aralkyloxy group, an (C6–C11)aryloxy group and a (C4–C6)cycloalkoxy group, an (C7–C11)aralkyl, (C6–C10)aryl or (C4–C6)cycloalkyl group all of which may be substituted with a group selected from an (C1–C8)alkyl group, an (C1–C8) alkoxy group, an (C7–C11)aralkyloxy group, an (C6–C11)aryloxy group, and a (C4–C6)cycloalkoxy group, $R_2$ represents a hydrogen atom, an (C1–C8)alkyl group, a (C4–C6)cycloalkyl group, or an (C7–C11)aralkyl or phenyl group which may be substituted with a group selected from an (C1–C8)alkyl group, an (C1–C8)alkoxy group, an (C7–C11) aralkyloxy group, an (C6–C11)aryloxy group and a (C4–C6)cycloalkoxy group, $X_1$ and $X_2$ are the same or different and independently represent a hydrogen atom, a halogen atom, a nitro group, an (C1–C8)alkyl group, an (C1–C4)alkoxy group or a cyano group, and two adjacent $X_1$ and $X_2$ together with the benzene ring to which they are bonded may form a 1-hydroxy-2- or 2-hydroxy-1-naphthyl group.

5. The chiral copper complex catalyst composition according to claim 4, wherein $X_1$ represents a chlorine atom, a bromine atom or a nitro group;

$X_2$ represents a hydrogen atom, a methyl group, a methoxy group, a chlorine atom, a fluorine atom or a bromine atom;

$R_1$ represents a (C1–C6)alkyl group, a phenyl group, a naphthyl group, a benzyl group or a naphthylmethyl group; and $R_2$ represents an (C1–C6)alkyl group, a benzyl group, a phenyl group, a 2-methoxyphenyl group, a 2-tert-butoxy-5-tert-butylphenyl group or a 2-octyl-5-tert-butylphenyl group.

6. The composition according to claim 1 or 3, wherein the mono-valent or di-valent copper compound is a copper salt of an organic carboxylic acid having 2 to 15 carbon atoms.

7. The composition according to claim 4, wherein the mono-valent or di-valent copper compound is a copper salt of an organic carboxylic acid having 2 to 15 carbon atoms.

8. The process for producing an optically active cyclopropane-carboxylic acid ester according to claim 2, wherein after contacting the optically active N-salicylideneaminoalcohol compound with the monovalent or di-valent copper compound in an inert solvent, the resulting mixture is contacted with a base, and is optionally washed with water and dehydrated.

9. The process for producing an optically active cyclopropane-carboxylic acid ester according to claim 2 or 8, wherein $R_1$ represents an (C1–C8)alkyl group which may be substituted with a group selected from an (C1–C4)alkoxy group, an (C7–C11)aralkyloxy group, an (C6–C11)aryloxy group and a (C4–C6)cycloalkoxy group, an (C7–C11)aralkyl, (C6–C10)aryl or (C4–C6)cycloalkyl group all of which may be substituted with a group selected from an (C1–C8)alkyl group, an (C1–C8) alkoxy group, an (C7–C11)aralkyloxy group, an (C6–C11)aryloxy group, and a (C4–C6)cycloalkoxy group, $R_2$ represents a hydrogen atom, an (C1–C8)alkyl group, a (C4–C6)cycloalkyl group, or an (C7–C11)aralkyl or phenyl group which may be substituted with a group selected from an (C1–C8)alkyl group, an (C1–C8)alkoxy group, an (C7–C11) aralkyloxy group, an (C6–C11)aryloxy group and a (C4–C6)cycloalkoxy group, $X_1$ and $X_2$ are the same or different and independently represent a hydrogen atom, a halogen atom, a nitro group, an (C1–C8)alkyl group, an (C1–C4)alkoxy group or a cyano group, and two adjacent $X_1$ and $X_2$ together with the benzene ring to which they are bonded may form a 1-hydroxy-2- or 2-hydroxy-1-naphthyl group.

10. A process for producing an optically active cyclopropane-carboxylic acid ester as recited in claim 9, wherein $X_1$ represents a chlorine atom, a bromine atom or a nitro group;

$X_2$ represents a hydrogen atom, a methyl group, a methoxy group, a chlorine atom, a fluorine atom or a bromine atom;

$R_1$ represents a (C1–C6)alkyl group, a phenyl group, a naphthyl group, a benzyl group or a naphthylmethyl group; and $R_2$ represents an (C1–C6)alkyl group, a benzyl group, a phenyl group, a 2-methoxyphenyl group, a 2-tert-butoxy-5-tert-butylphenyl group or a 2-octyl-5-tert-butylphenyl group.

* * * * *